United States Patent
Vasquez Quintero

(10) Patent No.: US 12,004,943 B2
(45) Date of Patent: Jun. 11, 2024

(54) ARTIFICIAL IRIS, A METHOD FOR CONTROLLING AN ARTIFICIAL IRIS, AN ARTIFICIAL IRIS, A METHOD FOR CONTROLLING AN ARTIFICIAL IRIS, AND A METHOD FOR DETERMINING A USER-SPECIFIC PROFILE FOR AN ARTIFICIAL IRIS AND A METHOD FOR DETERMINING A USER-SPECIFIC PROFILE FOR AN ARTIFICIAL IRIS

(71) Applicant: IMEC VZW, Leuven (BE)

(72) Inventor: Andres Felipe Vasquez Quintero, Antwerp (BE)

(73) Assignee: IMEC VZW, Leuven (BE)

( * ) Notice: Subject to any disclaimer, the term of this patent is extended or adjusted under 35 U.S.C. 154(b) by 636 days.

(21) Appl. No.: 17/128,097

(22) Filed: Dec. 19, 2020

(65) Prior Publication Data

US 2021/0186679 A1    Jun. 24, 2021

(30) Foreign Application Priority Data

Dec. 20, 2019 (EP) ..................... 19218776

(51) Int. Cl.
*A61F 2/14* (2006.01)
*G01J 1/42* (2006.01)
(Continued)

(52) U.S. Cl.
CPC .............. *A61F 2/14* (2013.01); *G01J 1/4204* (2013.01); *G02C 7/04* (2013.01); *G02F 1/13318* (2013.01);
(Continued)

(58) Field of Classification Search
None
See application file for complete search history.

(56) References Cited

U.S. PATENT DOCUMENTS 4,091,329 A    5/1978   Fletcher et al.
5,108,427 A    4/1992   Majercik et al.
(Continued)

FOREIGN PATENT DOCUMENTS

EP    1674049 A1    6/2006
EP    1970732 A2    9/2008
(Continued)

OTHER PUBLICATIONS

Roose et al., "An Active Artificial Iris Controlled by a 25-µW Flexible Thin-Film Driver", KULeuven, Leuven, Belgium, email: florian.deroose@imec.be, imec, Leuven, Belgium, UGent, Gent, Belgium, 2016.

(Continued)

*Primary Examiner* — Javier G Blanco
(74) *Attorney, Agent, or Firm* — MOSER TABOADA

(57) ABSTRACT

In some embodiments, a method for controlling an artificial iris may include receiving a measurement of light intensity detected by a sensor on or adjacent to the artificial iris. The method may include accessing a user-specific profile based on user calibration for determining one or more user-specific thresholds of light intensity of the user-specific profile. The one or more user-specific thresholds are associated with light intensities for triggering a change of light transmittance through the artificial iris. The method may include comparing the received measurement of light intensity to the one or more thresholds in the user-specific profile. The method may include determining, based on the comparing, whether to turn on or turn off one or more concentric rings of liquid crystals of the artificial iris for controlling an amount of light transmitted through the artificial iris.

17 Claims, 7 Drawing Sheets

(51) Int. Cl.

| | | |
|---|---|---|
| *G02C 7/04* | (2006.01) | |
| *G02F 1/133* | (2006.01) | |
| *G02F 1/137* | (2006.01) | |
| *G16H 10/60* | (2018.01) | |
| *G16H 40/40* | (2018.01) | |
| *G16H 40/67* | (2018.01) | |

(52) U.S. Cl.
CPC ............. *G02F 1/137* (2013.01); *G16H 10/60* (2018.01); *G16H 40/40* (2018.01); *G16H 40/67* (2018.01); *A61F 2250/001* (2013.01)

(56) References Cited

U.S. PATENT DOCUMENTS

| | | | |
|---|---|---|---|
| 5,155,353 | A | 10/1992 | Pahr |
| 5,329,206 | A | 7/1994 | Slotkowski et al. |
| 5,498,865 | A | 3/1996 | Gaboury et al. |
| 6,501,443 | B1 | 12/2002 | McMahon |
| 9,072,465 | B2 | 7/2015 | Pugh et al. |
| 9,612,456 | B1 | 4/2017 | Pugh et al. |
| 10,292,810 | B1* | 5/2019 | Haddock ............... A61F 2/1659 |
| 2004/0233383 | A1 | 11/2004 | Sandler et al. |
| 2008/0055541 | A1 | 3/2008 | Coulter et al. |
| 2009/0033863 | A1 | 2/2009 | Blum et al. |
| 2009/0204207 | A1 | 8/2009 | Blum et al. |
| 2013/0303921 | A1 | 11/2013 | Chu et al. |
| 2014/0081178 | A1 | 3/2014 | Pletcher et al. |
| 2017/0059883 | A1 | 3/2017 | Wiser |
| 2017/0097520 | A1 | 4/2017 | Lee |
| 2017/0354326 | A1 | 12/2017 | Pugh et al. |
| 2018/0246049 | A1 | 8/2018 | Gutierrez |
| 2018/0275424 | A1 | 9/2018 | Lee |

FOREIGN PATENT DOCUMENTS

| | | | |
|---|---|---|---|
| EP | 3125021 | A1 | 2/2017 |
| JP | S5737221 | A | 3/1982 |
| JP | H-04174566 | A | 6/1992 |
| JP | H-07135453 | A | 5/1995 |
| JP | H-11160659 | A | 6/1999 |
| JP | 2007201350 | A | 8/2007 |
| JP | 2008176681 | A | 7/2008 |
| JP | 2013513127 | A | 4/2013 |
| KR | 20130007128 | A | 1/2013 |
| KR | 20130141058 | A | 12/2013 |
| WO | WO-2013/059656 | A2 | 4/2013 |
| WO | WO-2014/064259 | A1 | 5/2014 |
| WO | WO-2014/138974 | A1 | 9/2014 |
| WO | WO-2014/194432 | A1 | 12/2014 |
| WO | WO-2017058401 | A1 | 4/2017 |
| WO | WO-2018111992 | A1 | 6/2018 |
| WO | WO-2020/234278 | A1 | 11/2020 |

OTHER PUBLICATIONS

Xu et al., "Interaction of aberrations, diffraction, and quantal fluctuations determine the impact of pupil size on visual quality", Journal of the Optical Society of America A, vol. 34, No. 4, Apr. 2017.

European Search Report for Application No. 19218776.3, dated Jun. 10, 2020.

Ando et al: "Light Attenuation by the Human Eyelid", Biol Psychiatry, 39, pp. 22-25, 1996.

Hsu et al: "Concentric polymer-dispersed liquid crystal rings for light intensity modulation", Sensors and Actuators A: Physical, vol. 169, No. 2, pp. 341-346, 2011.

Kwon et al: "High-speed camera characterization of voluntary eye blinking kinematics", Journal of the Royal Society Interface, 10, Feb. 27, 2013, pp. 1-6, 2013.

Andrés Felipe Vasquez Quintero et al: "Design and modelling of thermoformed displays for smart contact lenses", SID-ME fall meeting 2016, Berlin Conference Paper S5-1, p. 14-15.

Celine Vanhaverbeke et al: "A biocompatible active artificial iris", SID-ME fall meeting 2016, Berlin Conference Paper S5-2, p. 16-17.

Andrés Felipe Vasquez Quintero et al: "Stretchable platform enabled with wireless power for smart contact lenses", MRS Fall 2017, Boston, Conference Paper (Poster), 1 page.

Herbert De Smet et a: "Simple multifocal lens based on liquid crystals", EuroDisplay 2017, Berlin, EuroDisplay 2017 Conference Abstract Book, p. 49-50.

Vasquez Quintero et al: "Liquid crystal displays compatible with contact lenses for vision correction applications", International Display Workshop (IDW), IDW 2018, Conference Paper (Proceedings Paper), pp. 3, Japan, Nagoya, 2018.

Wikipedia: "Log amplifier", https://link.edgepilot.com/s/f15366f5/ZIYmxUK5zU6WXNYQdMbqgQ?u=https://en.wikipedia.org/w/index.php?title=Log_amplifier%26oldid=859414094, available on Sep. 13, 2018.

International Search Report and Written Opinion of the International Searching Authority in PCT/EP2020/063919 dated Aug. 26, 2020.

Allos, et al: "Novel low-cost ratiometric photometer", J. Phys. E: Sci. Instrum., vol. 11, 1978.

A de Sa and D G McCartan: "Ratiometric measurements in optical absorption Spectroscopy", J. Phys. E: Sci. Instrum. 9 725, (1976).

\* cited by examiner

ARTIFICIAL IRIS, A METHOD FOR CONTROLLING AN ARTIFICIAL IRIS, AN ARTIFICIAL IRIS, A METHOD FOR CONTROLLING AN ARTIFICIAL IRIS, AND A METHOD FOR DETERMINING A USER-SPECIFIC PROFILE FOR AN ARTIFICIAL IRIS AND A METHOD FOR DETERMINING A USER-SPECIFIC PROFILE FOR AN ARTIFICIAL IRIS

CROSS-REFERENCE TO RELATED APPLICATION

The present application is based on priority claimed on European Patent Application No. 19218776.3, filed on Dec. 20, 2019, the contents of which are incorporated herein by reference.

TECHNICAL FIELD

The present inventive concept relates to an artificial iris. In particular, the present inventive concept relates to controlling an artificial iris.

BACKGROUND

An artificial iris may be used as an implanted iris or as a contact lens which is worn in the eye. The artificial iris may help a user to control light being passed towards a retina.

The artificial iris may be used for controlling or optimizing the visual acuity of a user. The artificial iris may thus need to take into account the ambient lighting conditions and adapt the artificial iris to the lighting conditions. A well-controlled artificial iris may thus e.g. help a user to better read in various different ambient lighting conditions.

There is a need of providing a suitable control for an artificial iris such that the amount of light transmitted through the artificial iris fits the need of the user.

SUMMARY

It is an object of the present inventive concept to provide a control of an artificial iris that is suitable for the needs of a user to control light transmitted through the iris.

This and other objects of the present inventive concept are at least partly met by the invention as defined in the independent claims. Preferred embodiments are set out in the dependent claims.

According to a first aspect, there is provided a method for controlling an artificial iris, said method comprising: receiving a measurement of light intensity detected by a sensor on or adjacent to the artificial iris; accessing a user-specific profile based on user calibration for determining one or more user-specific thresholds of light intensity of the user-specific profile, wherein the one or more user-specific thresholds are associated with light intensities for triggering a change of light transmittance through the artificial iris; comparing the received measurement of light intensity to the one or more thresholds in the user-specific profile; and determining, based on said comparing, whether to turn on or turn off one or more concentric rings of liquid crystals of the artificial iris for controlling an amount of light transmitted through the artificial iris.

Thanks to the method, the controlling of an artificial iris may be adapted to be user specific. Different persons may have different sensitivity to light. Thus, by ensuring that control of the artificial iris is based on a user-specific profile, the control of the artificial iris may be adapted to the specific needs of the user so as to provide a well-functioning artificial iris to the user.

The control of the artificial iris may ensure that light transmittance through the artificial iris may also be adapted to the visual acuity or contrast sensitivity of the user, so as to take differences in perceived contrast into account in the control of the artificial iris.

The user-specific profile may be acquired by means of performing calibration measurements on the user. The user-specific profile may then be downloaded into a memory arranged on a carrier of the artificial iris so as to be accessible for controlling the artificial iris. The downloading of the user-specific profile may be done to a pre-manufactured artificial iris that is to be used by the user or may be done on manufacture of the artificial iris such that the artificial iris is manufactured for the particular user.

The one or more user-specific thresholds may be represented in various different manners. The thresholds may be represented as a value corresponding to a value (e.g. a voltage) read out from the sensor. However, the voltage value may vary at least slightly dependent on the particular sensor specimen used in the artificial iris. Thus, in such case, the thresholds may need to be adapted or calibrated to the sensor of the artificial iris. According to an alternative, the thresholds may be represented as an illuminance value, wherein a sensor measurement may be used to determine a corresponding illuminance value. In such case, the user-specific profile is not tied to a particular specimen of an artificial iris. It should also be understood that other alternatives of representing the thresholds associated with processing of the read-out sensor value may be used. For instance, the thresholds may be represented as a retinal illuminance value, such that the determined light intensity measured at a position of the sensor may need to be further converted to a corresponding retinal illuminance value.

The artificial iris may comprise one or more concentric rings of liquid crystals. The liquid crystals may be switched between at least two states, which may include an on state corresponding to the liquid crystal being substantially opaque and not transmitting light and an off state corresponding to the liquid crystal being substantially transparent and transmitting light incident thereon. It should be realized that the liquid crystals need not be completely opaque and transparent in the on and off states. Hence, the liquid crystals may be switched between at least two states having different levels of transmittance. The liquid crystals may then be switched at least between an on state and an off state having different levels of transmittance, such that the transmittance through the ring of liquid crystals is higher in the off state than in the on state. The transmittance of the concentric rings in the on and off states may be taken into account in the user-specific profile for relating the retinal illumination to the measured light intensity.

Each of the thresholds may be associated with a corresponding concentric ring such that the concentric ring may be turned on or off in relation to the measured light intensity being above or below the threshold. Also, different thresholds for turning the concentric ring on and turning the concentric ring off may be used so as to avoid that a concentric ring is frequently triggered to turn on and off if the light intensity is close to the threshold.

Having a large number of concentric rings may allow an artificial pupil size of the artificial iris to be changed between various different sizes. However, a large number of concentric rings may imply that the artificial iris is complex, which may increase manufacturing costs. Thus, in a simple embodiment, the artificial iris may comprise at least one ring, which may allow the artificial iris to define two different levels of light transmittance, one when the liquid crystals of the ring are in an on state and another when the liquid crystals of the ring are in an off state.

The method may be performed in a processing unit comprising a processor and a memory, which may be integrated on the artificial iris. The processor may receive measurements from a sensor (which may also be integrated on the artificial iris), may access the user-specific profile from the memory and may further perform the acts of comparing and determining for controlling an amount of light transmitted through the artificial iris.

In this regard, the processing unit may for instance comprise a general-purpose processing unit, which may be provided with instructions for performing the method for controlling an artificial iris. Alternatively, the processing unit may be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the processing unit.

However, it should be realized that the method may alternatively be performed in a processing unit which is external to the artificial iris. The artificial iris could include a wireless communication unit, which communicates with an external processing unit for receiving signals for controlling the artificial iris. For instance, the processing unit may be arranged in a device which may be worn by the user. Having the processing unit external to the artificial iris may decrease complexity of the artificial iris and manufacturing costs. It is foreseen that the artificial iris needs to be replaced at regular intervals, whereas a processing unit arranged in an external unit may be have a much longer lifetime. Also, a processing unit in an external unit may simplify receiving input or updates to the processing unit, e.g. for selecting a user-specific profile or for updating user-specific profiles as discussed below.

As used herein, the term "change of light transmittance through the artificial iris" may be used to change an effective pupil diameter of the artificial iris. Thus, by changing the number of concentric rings that are set to the on state or the off state, the amount of light being transmitted through the artificial iris may be changed, corresponding to a change of an effective pupil diameter. This may be referred to below as changing a "size of the artificial iris". However, it should be understood that some light may always be transmitted through an entire area defined by all of the one or more concentric rings, since the rings may not be completely opaque in the on state. When referring to the size of the artificial iris being changed, it should thus be understood that a size of an active area of the artificial iris being set to an off state to provide a high level of transmittance is changed.

According to an embodiment, the method further comprises receiving input for selecting one of a plurality of stored user-specific profiles to be active, each user-specific profile being associated with a same user, wherein said accessing comprises accessing the user-specific profile selected to be active.

Each user may have a plurality of user-specific profiles. Functionality of the artificial iris may need to be different if the user is e.g. doing exercise, reading, or driving a car. When reading, it may be important that high light intensity levels are received at the retina, which may not be as important when doing exercise (and the user may like not to receive too high light intensities at the retina). In the case of driving a car, the user may be exposed to very fast changes in lighting conditions, e.g. when the car enters or leaves a tunnel.

Thus, by having a plurality of stored user-specific profiles, the artificial iris may be adapted for supporting different functionalities in different lighting conditions and/or in different user situations. This increases versatility of the artificial iris.

The input for selecting a stored user-specific profile may be provided by the user. For instance, the user may provide input when the user is about to do a certain activity, such as reading. The input may alternatively be received by a sensor detecting a change in ambient lighting conditions, which may require a different profile to be used for ensuring a proper functionality of the artificial iris. However, the artificial iris should with a single profile be able to change light transmittance of the iris so as to handle changes in lighting conditions, but a change of profile may be useful if exceptional changes to ambient lighting conditions occur, such as during foggy weather, or detecting a spectrum of light to determine whether the user is in an office environment or outdoors.

The active profile may then be used in controlling the artificial iris for triggering changes of a size of the artificial iris through which light is transmitted. The plurality of user-specific profiles may differ from each other in that at least one of the user-specific thresholds has different values for different user-specific profiles.

According to an embodiment, the method further comprises receiving input for changing the user-specific profile by changing one or more user-specific thresholds of the user-specific profile.

This implies that the user-specific profile may be changed. For instance, the user-specific profile may need to be updated due to eye changes of the user (e.g. due to aging). Alternatively, the user-specific profile may need to be updated due to changes in efficiency of the rings of liquid crystal, so as to adapt the artificial iris to an aging of the artificial iris.

The changing of the user-specific profile may be based on a new user calibration being performed (e.g. to determine eye changes of the user). The changing of the user-specific profile may alternatively be based on sensor input, such as detecting changes in transmittance of the rings of liquid crystal in on and off states. Such changes may be detected by performing measurements in a controlled environment when the artificial iris is not worn by the user (e.g. if the artificial iris is worn as a contact lens).

The changing of the user-specific profile may alternatively be performed based on a user experiencing a non-satisfactory functionality of the artificial iris. The user may thus provide input based on such experience for increasing or decreasing at least one of the user-specific thresholds of the user-specific profile.

According to an embodiment, said receiving a measurement of light intensity comprises receiving measurements of light intensities for a plurality of different wavelength ranges, wherein said user-specific profile comprises one or more user-specific thresholds for each of the plurality of different wavelength ranges, and wherein said comparing comprises comparing each of the measurements of light intensities for a plurality of different wavelengths to the one or more thresholds for each of the plurality of different wavelength ranges in the user-specific profile.

Thus, spectral information of the light intensity may be received. This implies that the artificial iris may also be controlled in relation to spectral information. The wavelength ranges may be quite broad, such that the measurements of light intensities may comprise three measurements representing blue, green and red light, wherein the measurements may relate to wavelength ranges that have partial overlap. However, it should be realized that the wavelength ranges may be much narrower, such as 10-50 nm wide, such that measurements for a large number of narrow wavelength ranges may be received.

The spectral information may be used for controlling the artificial iris, such that the artificial iris may be controlled differently depending on the wavelength content of incident light. For instance, thresholds relating to blue light may be lower than thresholds relating to other wavelengths, such that the size of the artificial iris may be smaller for large intensities of blue light compared to corresponding intensities of green or red light. This may be used for preventing damage to the retina, since large exposure to blue light can damage light-sensitive cells in the retina.

According to a second aspect, there is provided a computer program product comprising computer-readable instructions such that when executed on a processing unit the computer-readable instructions will cause the processing unit to perform the method according to the first aspect.

Effects and features of this second aspect are largely analogous to those described above in connection with the first aspect. Embodiments mentioned in relation to the first aspect are largely compatible with the second aspect.

The computer program product may be provided on computer-readable media providing a tangible carrier for the computer program product.

According to an embodiment, the computer program product may be provided for enabling downloading to a processing unit. Thus, the computer program product may be received as a signal carrying the computer program product to the processing unit, e.g. in communication over a computer network.

According to a third aspect, there is provided an artificial iris, said artificial iris comprising: a carrier, configured to be arranged in contact with a human eye or implanted in a human eye; a plurality of concentric rings of liquid crystals arranged on the carrier, wherein the liquid crystals are switchable between a blocking state providing a low transmittance of light through the artificial iris and a transmitting state providing a high transmittance of light through the artificial iris; a sensor arranged on the carrier, for detecting a light intensity incident on the artificial iris; and a processing unit comprising a processor and a memory, said memory storing at least one user-specific profile based on user calibration, each user-specific profile being associated with the same user, said processor being configured to: receive a measurement of light intensity detected by the sensor; access one of the at least one user-specific profile for determining one or more user-specific thresholds of light intensity of the user-specific profile, wherein the one or more user-specific thresholds are associated with light intensities for triggering a change of light transmittance through the artificial iris; compare the received measurement of light intensity to the one or more thresholds in the user-specific profile; and determine, based on said comparing, whether to turn on or turn off one or more of the concentric rings of liquid crystals for controlling an amount of light transmitted through the artificial iris.

Effects and features of this third aspect are largely analogous to those described above in connection with the first and second aspects.

Embodiments mentioned in relation to the first and second aspects are largely compatible with the third aspect.

The artificial iris provides a self-contained system on a carrier to be arranged in contact with a human eye (like a contact lens) or implanted in the human eye. The artificial iris is able to detect light intensities as input and to determine which rings of liquid crystals are to transmit light for controlling an amount of light transmitted through the artificial iris.

The memory may store the at least one user-specific profile such that the artificial iris may be configured to provide functionality for controlling an amount of light transmitted through the artificial iris that is fit for the specific user of the artificial iris.

The liquid crystals may be switched between at least two states having different light transmittance characteristics. The liquid crystals may not be completely opaque and completely transparent in the two states. As used herein, the term "blocking state" and "transmitting state" should be construed as corresponding to states of lower and higher transmittance of light, respectively, but the liquid crystals may not completely block light in the blocking state and may not be completely transparent in the transmitting state.

According to an embodiment, a width of one or more of the plurality of concentric rings is based on user calibration.

The user calibration may determine a desired pupil diameter for ensuring a good visual acuity in relation to different luminance levels. Based on the user calibration, the desired width of the one or more concentric rings may be determined. The width(s) may be selected to ensure that the artificial iris will function well for the user.

Also, a number of concentric rings of the artificial iris may be based on user calibration. Typically, if a large width of the concentric rings may be used, fewer concentric rings may be needed.

A reduced number of rings may typically be desired in order to decrease number of necessary interconnections between a control unit and the liquid crystal rings. Also, a reduced number of rings may reduce or prevent diffraction in boundaries between rings. Further, in boundaries between rings, there may be a small space with no liquid crystals present, where no switching between transmittance/blocking may occur. Thus, reducing the number of rings, contrast of the artificial iris may be increased.

An increased number of rings may ensure that the artificial iris may be changed between many different effective sizes to fit different luminance levels. Thus, with an increased number of rings, the size of the artificial iris may be set to closely fit a desired pupil diameter for various different luminance levels.

Using the user calibration, a decision on the width of the rings may be taken to ensure that the function of the artificial iris is adequate taking into account that good function for different luminance levels should be supported (many rings, small width) while the artificial iris should provide e.g. a good contrast (few rings, large width).

Once a width of the concentric rings has been selected, the artificial iris may be manufactured using the selected width parameter. Hence, the artificial iris may be manufactured to fit the user requirements.

According to an embodiment, the width of the concentric rings is non-equal.

According to a separate aspect, there is provided an artificial iris, said artificial iris comprising: a carrier, configured to be arranged in contact with a human eye or implanted in a human eye; a plurality of concentric rings of liquid crystals arranged on the carrier, wherein the liquid crystals are switchable between a blocking state providing a low transmittance of light through the artificial iris and a transmitting state providing a high transmittance of light through the artificial iris, wherein a width of at least two of the concentric rings of liquid crystals is non-equal.

An artificial iris having non-equal widths of the concentric rings may be advantageous in some situations. Thus, using non-equal widths of the concentric rings, options for design of the artificial iris to fit user requirements, such as light sensitivity of the user, may be increased.

The use of non-equal widths of the concentric rings may allow the artificial iris to be accurately controlled in a first range of luminance levels (by turning on/off narrow rings that have a small effect on the size of the artificial iris). However, since non-equal widths are used, the accurate control may be achieved without requiring a very large number of rings, such that the artificial iris only provides coarse control in a second range of luminance levels different from the first range. The arrangement of the concentric rings may be provided so that the artificial iris is configured to utilize narrow rings to control the size of the iris for a range of luminance levels in which it is desired to have accurate control.

An artificial iris having non-equal widths may be useful on its own, without necessarily being combined with user-specific profiles for controlling amount of light transmitted through the artificial iris.

It should be understood that some of the concentric rings may have similar (equal) width, even though at least two of the concentric rings have non-equal widths.

The artificial iris having non-equal widths of concentric rings may also comprise a sensor for detecting a light intensity incident on the artificial iris. This sensor could be arranged on the carrier. However, this sensor need not necessarily be placed on the carrier of the artificial iris. Rather, the sensor may be placed on a separate device, which may e.g. be worn close to the eye of the user for detecting a representative measurement of the light intensity incident on the artificial iris.

The artificial iris having non-equal widths of concentric rings may also comprise a processing unit comprising a processor and a memory, said processor being configured to: receive a measurement of light intensity detected by the sensor; compare the received measurement of light intensity to one or more thresholds; and determine, based on said comparing, whether to turn on or turn off one or more of the concentric rings of liquid crystals for controlling an amount of light transmitted through the artificial iris.

The processing unit may be arranged on the carrier, but may alternatively be arranged in a separate unit external to the artificial iris. The processing unit may use default thresholds for turning on or off one or more of the concentric rings, but may of course alternatively use user-specific thresholds according to user-specific profiles.

According to an embodiment, the width of the concentric rings is increasing towards outer rings.

In an embodiment, each concentric ring may have an equal or larger width than an inner ring neighbor. In another embodiment, each concentric ring may have a larger width than an inner ring neighbor.

Users having a high light sensitivity could benefit from an artificial iris with increasing widths for outer rings, since a size of the artificial iris may be fine-tuned for high luminance values.

According to another embodiment, the width of the concentric rings is decreasing towards outer rings.

In an embodiment, each concentric ring may have an equal or smaller width than an inner ring neighbor. In another embodiment, each concentric ring may have a smaller width than an inner ring neighbor.

Users having a low light sensitivity could benefit from an artificial iris with increasing widths for inner rings, since a size of the artificial iris may be fine-tuned for low luminance values.

According to another embodiment, the width of a set of concentric rings arranged between innermost and outermost rings may be smaller than the width of the innermost and outermost rings.

The set of concentric rings arranged between innermost and outermost rings may comprise at least two concentric rings. The width of the concentric rings in the set of concentric rings may or may not be equal.

This implies that coarse control of the size of the artificial iris may be provided for high and low luminance levels, whereas for a central range of luminance levels a fine-tuning of the size of the artificial iris is provided. This may be useful for users with optimal contrast sensitivity for a particular range of luminance levels (and associated sizes of the artificial iris).

According to a fourth aspect, there is provided a method for determining a user-specific profile for an artificial iris, said method comprising: receiving user-specific results of optimal pupil diameter for a plurality of different light intensities; fitting the user-specific results to form a representation of desired pupil diameter in relation to light intensity; determining a plurality of user-specific thresholds forming a user-specific profile, each user-specific threshold defining a minimum light intensity at which a concentric ring of liquid crystals in the artificial iris is to be turned on providing a low transmittance of light through the artificial iris, wherein each of the user-specific thresholds is determined based on using the formed representation to determine a light intensity associated with a pupil diameter corresponding to the concentric ring being turned on.

Effects and features of this fourth aspect are largely analogous to those described above in connection with the first, second, and third aspects. Embodiments mentioned in relation to the first, second, and third aspects are largely compatible with the fourth aspect.

It is an insight of the present inventive concept that user-specific profiles may provide an improvement in controlling an artificial iris of a user. According to the fourth aspect, a method for determining the user-specific profile is provided. The method includes receiving results of optimal pupil diameter for several different light intensities. Thus, by having user-specific input on optimal pupil diameter for different light intensities, the results may be fitted to a representation relating pupil diameter to light intensity. Then, this representation may be used for determining user-specific thresholds relating a pupil diameter corresponding to a concentric ring of an artificial iris being turned on to a light intensity level. Thus, user-specific thresholds may be determined for pupil diameters that lie in-between pupil diameters provided in the received user-specific results.

The user-specific results may be used for determining a plurality of parameters relating to providing an artificial iris that is adapted to the specific needs of a user. For instance, the user-specific results may be used for determining a suitable arrangement of concentric rings of the artificial iris (number of rings, widths of rings) and, once a decision of the design of the rings has been taken, the user-specific thresholds associated with each of the rings may be determined. Alternatively, user-specific thresholds may be determined for a pre-set configuration of the concentric rings (e.g. if only one design option of the concentric rings is allowed).

By determining user-specific thresholds, the control of the artificial iris may be adapted to the needs of the user.

The user-specific results of optimal pupil diameter may be based on tests performed on the user. Such tests may include a user providing subjective input as to what would be an optimal pupil diameter for a particular ambient light intensity. The pupil diameter may be varied e.g. using a pupil in front of the eye of the user.

The user-specific results may be based on an attempt to optimize one or more particular parameters for providing a desired functionality of the artificial iris being controlled based on the user calibration. For instance, a user may provide subjective input in relation to a particular parameter, such as light sensitivity, visual acuity or axial resolution experienced by the user during user calibration. Such parameters may also be subjectively mixed into a user input of optimal pupil diameter. The user-specific results may also be based on optimizing the one or more parameters in particular ambient lighting conditions, such as for particular color or wavelength content of ambient light and/or in bright/dark environments.

Fitting the user-specific results to form a representation of desired pupil diameter in relation to light intensity may be performed in many different manners. The user-specific results of desired pupil diameter may be plotted against light intensity to determine the representation, which may then be used for determining a plurality of user-specific thresholds. Alternatively, a function relating the desired pupil diameter to the light intensity may be determined. The representation of desired pupil diameter in relation to light intensity need not perfectly match the user-specific results. Rather, a plot or a determined function may be set to reduce an error between the representation and the user-specific results while e.g. using a particular type of representation (a particular function). Also, outlier results among the user-specific results may be ignored.

According to an embodiment, said fitting comprises determining a hyperbolic tangent function of desired pupil diameter in relation to a logarithm of light intensity, as measured in $Cd/m^2$.

It is realized that a hyperbolic tangent function may be used for providing a close fit between desired pupil diameters in relation to a logarithm of light intensity. Thus, using the hyperbolic tangent function, a relatively simple relation may be formed while closely fitting the desired pupil diameter to light intensity.

The fitting may comprise determining parameters for defining the hyperbolic tangent function so as to suit the user-specific results.

According to an embodiment, each user-specific threshold is determined to represent a threshold light intensity incident on a sensor that is arranged radially displaced from and adjacent to the concentric rings, said threshold light intensity corresponding to the minimum light intensity being transmitted through the artificial iris when the concentric ring is turned off.

Thus, the user-specific thresholds determined by the user calibration may be adapted to the light intensity incident on a sensor. This implies that a detected light intensity by a sensor may be directly compared to the user-specific threshold and that there is no need to convert the detected light intensity to the light intensity transmitted through the artificial iris. Hence, the user calibration may ensure that processing of the detected light intensity during use of the artificial iris is limited.

However, it should be understood that representing the user-specific threshold as a light intensity incident on a radially displaced sensor ties the user-specific threshold to the placement of the sensor, which may be varied between different types of artificial irises. Therefore, the user calibration may initially determine user-specific thresholds representing a light intensity being transmitted through the artificial iris. Such user calibration may then be used for determining, during manufacturing of an artificial iris, user-specific thresholds for the specific placement of the sensor used in the manufactured artificial iris. In other embodiments, the user calibration is performed for a known placement of the sensor in the artificial iris such that the user-specific thresholds may be immediately be determined during user calibration.

According to an embodiment, the method further comprises selecting a width of each of the concentric rings based on said user-specific results, said selected widths defining a pupil diameter corresponding to each of the concentric rings.

Thus, the user-specific results may be used for determining a suitable arrangement of concentric rings of the artificial iris (number of rings, widths of rings). In some embodiments, each of the concentric rings may has an equal width and in other embodiments, at least two of the concentric rings have non-equal widths.

Different settings of the widths of concentric rings may suit different users. A narrower width of the concentric rings may enable a more accurate control of the size of the artificial iris, so a decision of a width of concentric rings may be taken based on a needed accuracy of control.

Also, in particular circumstances, different settings for non-equal widths of the concentric rings may be used. For instance, first user-specific settings may be suitable for users having a high light sensitivity, second user-specific settings may be suitable for users having a low light sensitivity and third user-specific settings may be suitable for users having optimal contrast sensitivity for a particular range of luminance levels.

According to an embodiment, the method further comprises selecting a set-up of widths of the concentric rings from a plurality of default set-ups based on said user-specific profiles.

Having default set-ups may allow a manufacturer to support a pre-determined finite number of set-ups of the concentric rings of an artificial iris. Thus, the manufacturer may manufacture artificial irises using the default set-ups without taking user settings into account during manufacture. This allows the manufacturer to have finite number of versions of a product, so as to simplify managing manufacture and product versions.

A pre-manufactured artificial iris may then be provided with user calibration so as to adapt the artificial iris to the needs of the user. A decision of which type of default set-up that may fit the user may be taken based on result of the user calibration.

According to an embodiment, said method comprises receiving at least two sets of user-specific results of optimal pupil diameter for a plurality of different light intensities, each of the at least two sets representing a different condition for the same user; performing the fitting and the determining for each of the at least two sets of user-specific results to form plural user-specific profiles for the same user.

Each user may have a plurality of user-specific profiles. Functionality of the artificial iris may need to be different if the user is e.g. doing exercise, reading, or driving a car. When reading, it may be important that high light intensity levels are received at the retina, which may not be as important when doing exercise (and the user may like not to receive too high light intensities at the retina). In the case of driving a car, the user may be exposed to very fast changes in lighting conditions, e.g. when the car enters or leaves a tunnel.

Thus, by receiving at least two sets of user-specific profiles, the artificial iris may be adapted for supporting different functionalities in different lighting conditions and/or in different user situations. This increases versatility of the artificial iris.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
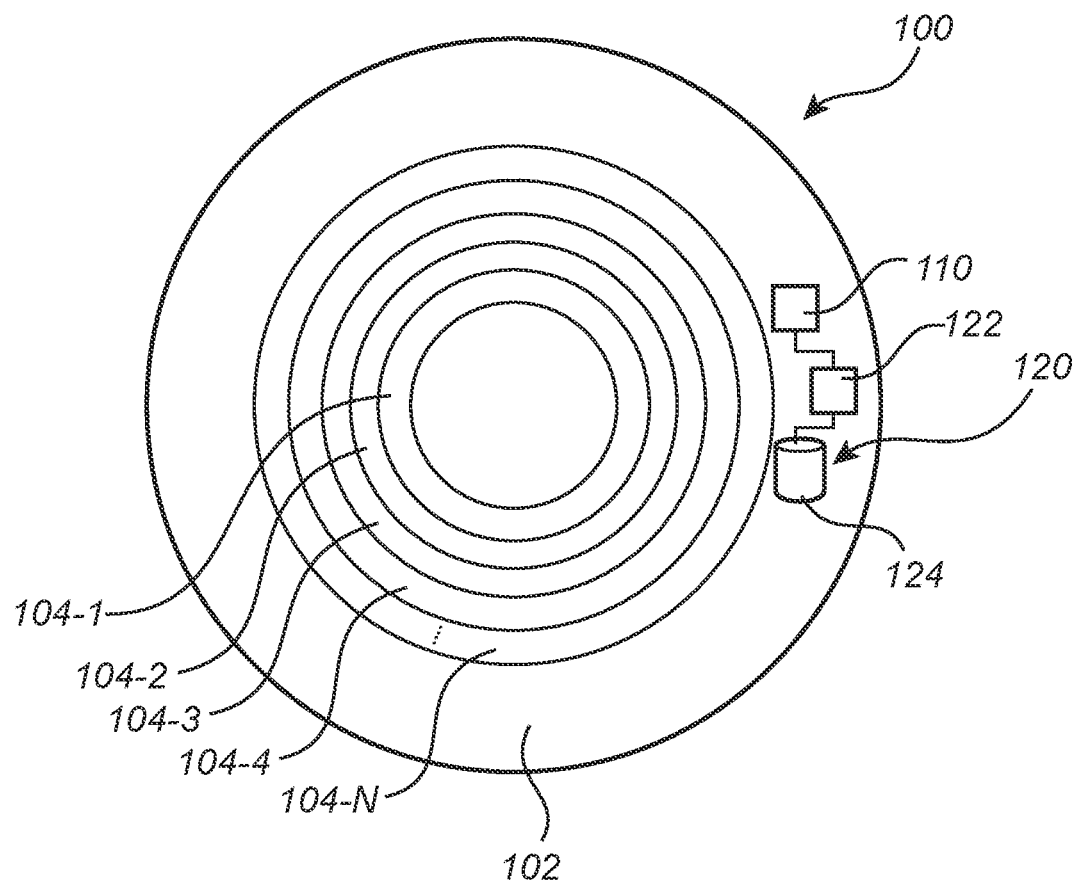
FIG. 1 is a schematic view of an artificial iris according to an embodiment.

Referring to FIG. 1, an artificial iris 100 is illustrated. The artificial iris 100 may be used as an implanted iris or as a contact lens which is worn in the eye. The artificial iris 100 may help a user to control light being passed towards a retina.

The artificial iris 100 may comprise a carrier 102, configured to be arranged in contact with a human eye or implanted in a human eye. The carrier 102 may provide a substrate for carrying components of the artificial iris 100. The artificial iris 100 may be shaped to fit being worn on or implanted in an eye or may be flexible so as to conform to the shape of the eye. The artificial iris 100 may thus e.g. be formed by a plastic material or a hydrogel material as is currently used in contact lenses. The carrier 102 may be transparent so as not to affect vision of the user.

The artificial iris 100 may further comprise a plurality of concentric rings 104-1 to 104-N (where N is an integer such that N>1). The rings 104-1 to 104-N are concentrically arranged. The rings 104-1 to 104-N may have different inner/outer diameters, and for example be arranged such that the smallest ring (e.g. the ring 104-1) is at the center and the other rings (e.g. 104-2 to 104-N) are arranged outwards of the ring 104-1 in order of increasing diameters. Each ring 104-1 to 104-N may be operable between a state having a lower attenuation of light (e.g. a "transmitting state") and a state having a higher attenuation of light (e.g. a "blocking state").

The state of each ring 104-1 to 104-N may be set providing a control signal to a dedicated control circuitry for controlling the respective ring 104-1 to 104-N.

Inside the smallest ring 104-1, there may be a transparent circular area, corresponding to a smallest pupil diameter of the artificial iris 100. Thus, a size of the pupil diameter defined by the artificial iris 100 may be varied between a smallest diameter corresponding to the diameter of the transparent circular area (when all rings 104-1 to 104-N are set to the blocking state) and a largest diameter corresponding to the diameter of the largest ring 104-N (when all rings 104-1 to 104-N are set to the transmitting state). However, in an embodiment, the innermost circular area may also be provided with liquid crystals such that it may be switched between a transmitting state and a blocking state.

In some embodiments, the rings 104-1 to 104-N may for example be of a twisted nematic (TN) or super twisted nematic (STN) type. In other embodiments, the one or more rings 104-1 to 104-N may be of a guest-host liquid crystal type, including a mix of e.g. a color dichroic dye, chiral dopant and liquid crystal. Such a type may be beneficial in that it may not need a polarizer to filter light. Such a type may also be driven in a direct current (DC) manner instead of an alternating current (AC) manner. Driving the one or more rings 104-1 to 104-N in a DC manner may further reduce energy consumption, and thereby help to further reduce e.g. a battery capacity needed for driving the artificial iris 100. It is envisaged also that rings of one or more other types than liquid crystal display (LCD) type may be used, as long as a same or similar functionality is obtained.

The artificial iris 100 may further comprise a sensor 110 on the carrier 102. The sensor 110 may be configured for detecting a light intensity incident on the artificial iris 100. The sensor 110 may for example be a photodiode, photodetector or photosensor, or another element (i.e. a photosensitive device) which may provide a photocurrent through it as a function of the intensity and/or wavelength of the incident light or which may accumulate charges as a function of the intensity and/or wavelength of the incident light.

The artificial iris 100 may be inserted into an eye of a user (not shown) such that the rings 104-1 to 104-N obtains the function of an artificial iris of the eye, and such that the sensor 110 is at least partly covered by an eye lid of the eye when the eye lid is partially or completely closed. The artificial iris 100 may further be configured such that, when inserted into the eye of the user, as much of the artificial iris 100 except the rings 104-1 to 104-N are arranged outside a field of visibility for the eye, in order not to disturb the sight of the user more than necessarily.

The artificial iris 100 may include a processing unit 120, which may be arranged on the carrier 102. The processing unit 120 is configured to operate the rings 104-1 to 104-N (i.e. to operate each ring between its transmitting and blocking states, as needed) based on an intensity of an incident light hitting the light sensor 110, thereby together with the rings 104-1 to 104-N emulating the functioning of an iris.

A size of the artificial iris 100, i.e. a size of an area that provides a high level of transmittance of light towards the retina of the user, may be controlled by the number of rings being set to the transmitting state. The rings being set to the transmitting state define a combined area which forms the size of the artificial iris 100. Widths of the rings 104-1 to 104-N thus define how accurately the size of the artificial iris 100 may be controlled. All rings 104-1 to 104-N may have equal widths. However, some rings 104-1 to 104-N may be wider or narrower so as to define luminance levels for which coarse or accurate control is desired, also taking into account that if narrow rings are used the number of rings will increase which will increase complexity of circuitry for controlling the rings 104-1 to 104-N.

The processing unit 120 may be configured to operate the rings 104-1 to 104-N based on a user-specific profile. The user-specific profile may be based on user calibration and may ensure that the artificial iris 100 is adapted to user requirements. The artificial iris 100 may also have widths of rings 104-1 to 104-N based on user-specific requirements.

The processing unit 120 may comprise a processor 122 for processing instructions for controlling the rings 104-1 to 104-N. The processing unit 120 may further comprise a memory 124, which may store the user-specific profile so as to enable the processor 122 to access the user-specific profile and allow the processor 122 to control the rings 104-1 to 104-N based on the user-specific profile.

The processor 122 may be configured to receive a measurement of light intensity detected by the sensor 110. The measurements of light intensity may be provided at regular intervals for ensuring continuous control of the artificial iris 100. The processor 122 may be configured to receive a measurement of light intensity only when a measurement of light intensity is changed, so as to avoid processing to be performed when conditions are not changed and no change in controlling the rings 104-1 to 104-N may be needed. Alternatively, the processor 122 may initially check whether the received measurement of light intensity differs from a preceding value so as to determine whether further processing is needed.

The processor 122 may further be configured to access a user-specific profile in the memory 124. The memory 124 may store a single user-specific profile which is always to be used by the processor 122. However, in an embodiment, the memory 124 may store a plurality of user-specific profiles. Each profile may be associated with the same user and different profiles may e.g. be adapted for controlling the artificial iris 100 in different conditions, such as different lighting conditions or for different activities of the user. The processor 122 may thus receive input (e.g. manual input from a user or based on a sensor input) relating to which user-specific profile that should be used.

The accessed user-specific profile may define one or more user-specific thresholds of light intensity of the user-specific profile. The one or more user-specific thresholds may be associated with light intensities for triggering a change of a size of the artificial iris 100 through which light is transmitted with a high transmittance.

The processor 122 may then compare the received measurement of light intensity to the one or more thresholds in the user-specific profile. The user-specific threshold may be provided as a value which may be directly compared to the received measurement of light intensity, such that the user-specific threshold may e.g. be adapted to a placement of the sensor 110 on the carrier 102. However, the user-specific threshold and the received measurement of light intensity may alternatively represent different light intensities (such as a light intensity received at a retina of the user and a light intensity received at the sensor 110). In such case, the processor 122 may be configured to process one or more of the received measurement of light intensity and the user-specific thresholds so that values of the received measurement and the user-specific threshold represent a common property. Then, the processor 122 may compare the received measurement to the user-specific thresholds to determine whether the received measurement is above or below one or more of the user-specific thresholds.

The processor 122 may further be configured to determine, based on said comparing, whether to turn on (i.e. set to blocking state) or turn off (i.e. set to transmitting state) one or more of the concentric rings of liquid crystals for controlling an amount of light transmitted through the artificial iris. Thus, if the received measurement is above a threshold of a ring (i.e. the amount of incident light is above the threshold), the concentric ring may be turned on to decrease the size of the artificial iris 100. The processor 122 may output a control signal to control circuitry for controlling the respective ring 104-1 to 104-N based on determining that a concentric ring 104-1 to 104-N is to be turned ON or OFF.

The processor 122 may for instance comprise a general-purpose processing unit, which may be provided with instructions for controlling the artificial iris 100. Alternatively, the processor 122 may be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the processor 122.

The instructions for controlling the artificial iris 100 may be provided in form of software, which may be separately delivered, and which may be loaded to an existing artificial iris 100 for improving functionality of the artificial iris 100.

It should also be realized that the sensor 110 and the processing unit 120 need not necessarily be arranged on the carrier 102 of the artificial iris 100. Alternatively, the sensor 110 and/or the processing unit 120 may be arranged in one or more separate units, which may or may not also be worn by the user. Thus, the processing unit 120 may be configured to communicate control signals to the artificial iris 100 (e.g. to a wireless communication unit of the artificial iris 100) for controlling the rings 104-1 to 104-N. This may limit complexity of electronic circuitry on the artificial iris 100 so that a price of the artificial iris 100 may be reduced. Also, processing performed on the artificial iris 100 may be limited so as to ensure long battery time.

Now, a method for determining a user-specific profile for an artificial iris 100 will be described.

The user-specific profile defines user requirements for controlling a diameter of an aperture (effective pupil size of the artificial iris 100). The user-specific profile may be defined in relation to specific user requirements (such as light sensitivity, visual acuity, quantal fluctuations, axial resolution, color/wavelength of light, bright/dark environments, etc.).

The user-specific profile may then be used together with ambient luminance level to control an amount of light reaching the eye (retinal illuminance) based on dimensions and numbers of rings 104-1 to 104-N, the rings' transmittance and state.

The user calibration may be used for configuring an artificial iris 100. The configuration may provide a hardware implementation, i.e. changing widths of the rings 104-1 to 104-N. The configuration may also provide settings to be used by the processing unit 120 (i.e. providing user-specific threshold values).

The user-specific profile may be based on user calibration measurements. These measurements may provide user-specific results, which may be received as input to determining a user-specific profile.

The received measurements may be performed per user or even per eye of the user. The measurements may be performed to determine an optimal pupil diameter for a plurality of different ambient light intensities. The optimal pupil diameter may be determined in dependence of a desired parameter (or a combination of parameters) to be controlled, such as light sensitivity, visual acuity, quantal fluctuations, color/wavelength, axial resolution, bright/dark environments, etc.

A plurality of measurements may also be used for different parameters, such that a plurality of user-specific profiles may be formed, each for a different parameter (or combination of parameters). Thus, depending on which parameter to be optimized when using the artificial iris 100, the corresponding user-specific profile may be used.

The optimal pupil diameter may be determined in dependence of a particular activity of the user, such as reading, doing exercise, or driving a car. Thus, user-specific profiles adapted for different activities of the user may also be determined.

The user-specific results may be obtained by changing luminance level and determining an optimal pupil diameter for the luminance level. Thus, at each luminance level, the pupil diameter may be changed in order to determine the optimal pupil diameter. The pupil diameter may be changed by dilating the pupil and/or using a pupil in front of the eye of the user during measurements. The user may provide subjective input to define an optimal pupil diameter, e.g. to define an optimal contrast (visual acuity) at the luminance level or to define an experience of light level in relation to light sensitivity at the luminance level. Alternatively, a reaction of the user to each pupil diameter at the luminance level may be measured so as to determine the optimal pupil diameter.

The user-specific results may then be fitted to form a representation of desired pupil diameter in relation to light intensity.

The pupil diameters may be fitted with a hyperbolic tangent (TAN H) function. TAN H functions may be suitable for properly fitting a relationship between pupil diameter and luminance for an eye.

Figure 2:
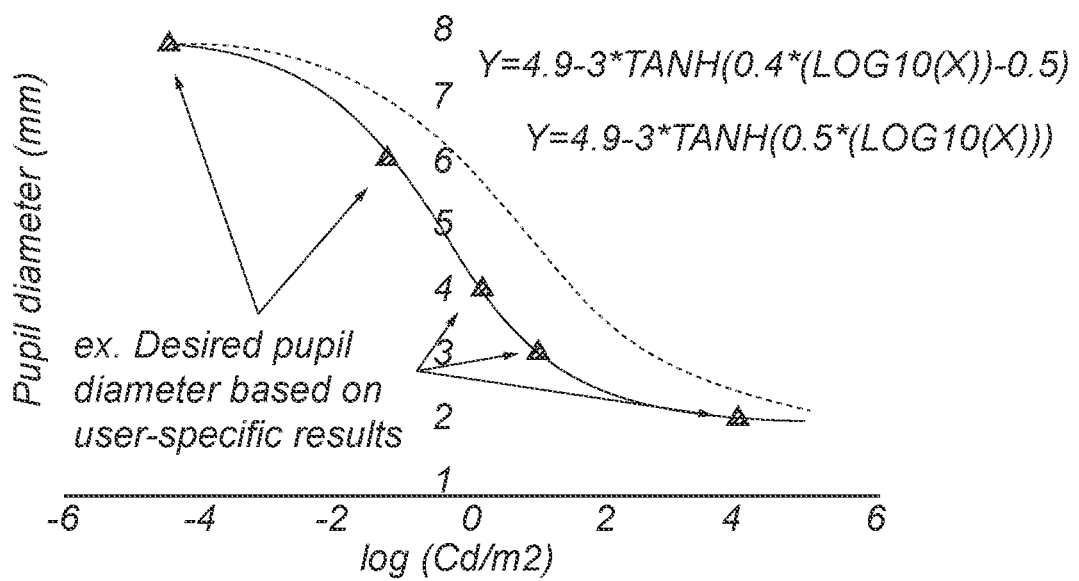
FIG. 2 is a diagram illustrating a relation between desired pupil diameter and light intensity.

In FIG. 2, a desired pupil diameter in mm versus logarithm to base 10 of luminance in cd/m$^2$ is plotted. The desired pupil diameter is plotted between a maximal pupil diameter of 8 mm to a minimal pupil diameter of 2 mm. Typically, the pupil diameter may not be varied beyond these diameters.

The dashed curve in FIG. 2 shows an average optimal pupil diameter of a human eye, which can be modeled by the TAN H equation $$\text{Pupil diameter}=4.9-3*\text{TAN } H(0.4*(\text{LOG}(X))-0.5)^2,$$

where X is the luminance in cd/m$^2$ and LOG is the logarithm function to base 10.

The solid triangles in FIG. 2 represent an example of desired pupil diameter for a specific eye based on user-specific results. In this example, every desired pupil diameter is smaller for the same luminance compared to the average curve, illustrating that use of average pupil diameters of an eye will not suit the user and will generally provide a too high light intensity to be transmitted to the retina. The points defined by the solid triangles may be fitted to a representation of the desired pupil diameter in relation to light intensity. The points can also be fitted by a TAN H equation, illustrated by the solid curve in FIG. 2. In this case, a user-specific calibration curve may be determined as $$\text{Pupil diameter}=4.9-3*\text{TAN } H(0.5*(\text{LOG}(X))).$$

Based on this calibration curve, all the possible desired diameters versus luminance levels may be calculated for this specific user.

It should be realized that a representation of the desired pupil diameter in relation to light intensity for the specific user may be determined in many different ways. Thus, the representation may be determined by plotting the calibration curve as discussed above. However, the representation may be determined by merely calculating a function to represent the desired pupil diameter in relation to light intensity based on user-specific results without necessarily plotting the results. Also, other functions may be determined, e.g. by forming separate functions of desired pupil diameter in relation to light intensity between adjacent measurement points, or by fitting a function to the user-specific results without requiring the function to perfectly match the user-specific results. For instance, if a TAN H function may not perfectly match the user-specific results, a representation using the TAN H function may be determined by e.g. minimizing a least-square error between the TAN H function and the user-specific results.

Based on the user-specific results, width and number of rings 104-1 to 104-N may be determined. The width and number of rings 104-1 to 104-N may be freely determined in order to fit the user requirements, while also taking into account that a reduced number of rings may typically be desired in order to decrease interconnections to the rings 104-1 to 104-N for controlling the state of the liquid crystals, to prevent or reduce diffraction in boundaries between rings 104-1 to 104-N and to decrease negative impact on contrast of the artificial iris 100 based on a small space with no liquid crystals being arranged between rings 104-1 to 104-N.

Referring now to FIGS. 3-6, four different embodiments of width profiles of the concentric rings 104-1 to 104-N are provided to illustrate the differences and benefits of changing the width of the concentric rings 104-1 to 104-N.

It should also be realized that the user-specific results may be used for choosing a particular width profile based on a set of pre-determined default set-ups. For instance, the width profiles illustrated in FIGS. 3-6 may be provided with a few different settings of the widths of the respective width profiles. Then, a suitable set-up for the user may be selected from these default set-ups to fit the user requirements.

Figure 4:
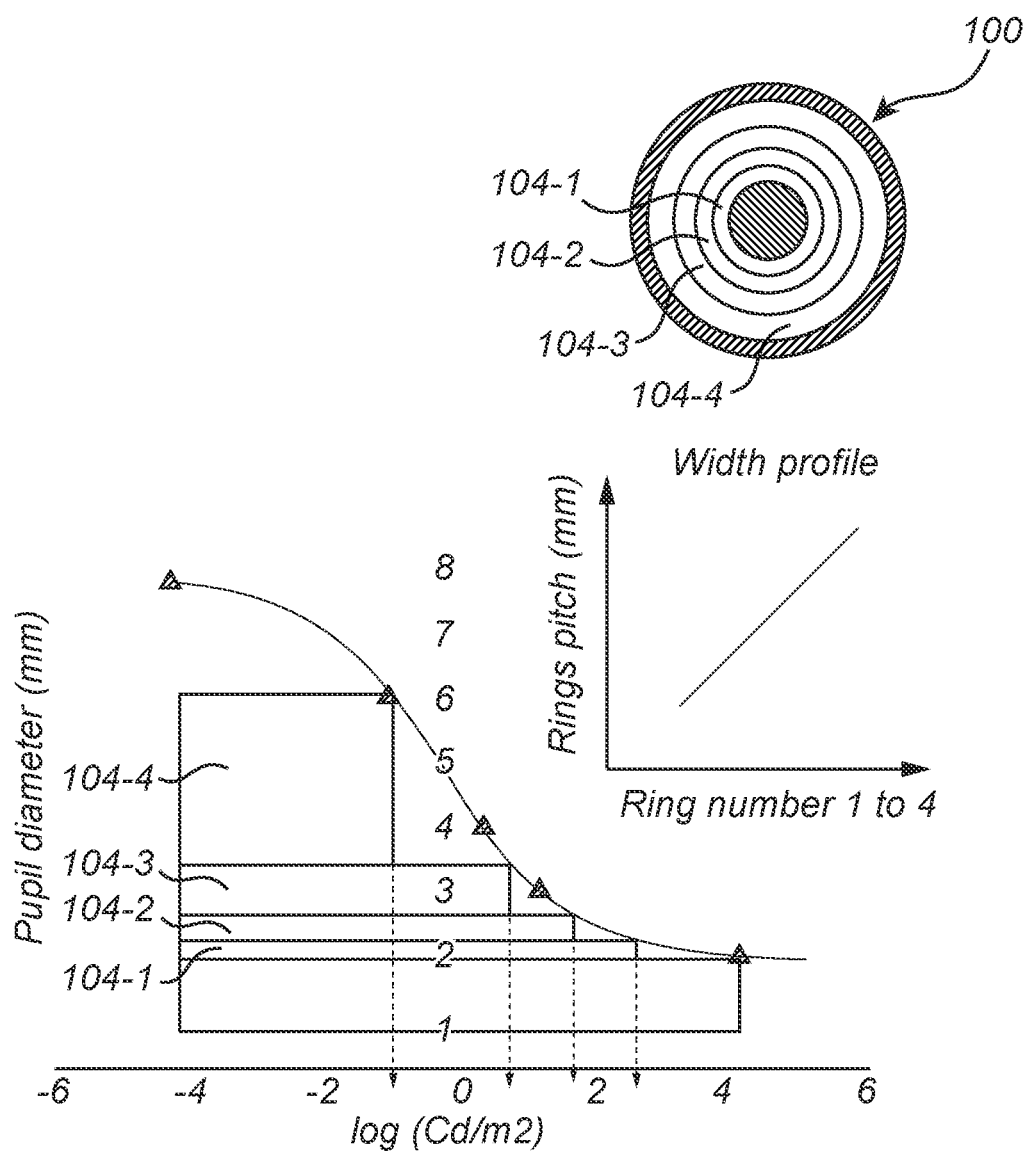
FIG. 4 schematically illustrates a width profile of concentric rings of liquid crystals of an artificial iris according to a second embodiment and user-specific thresholds associated with the rings.
Figure 5:
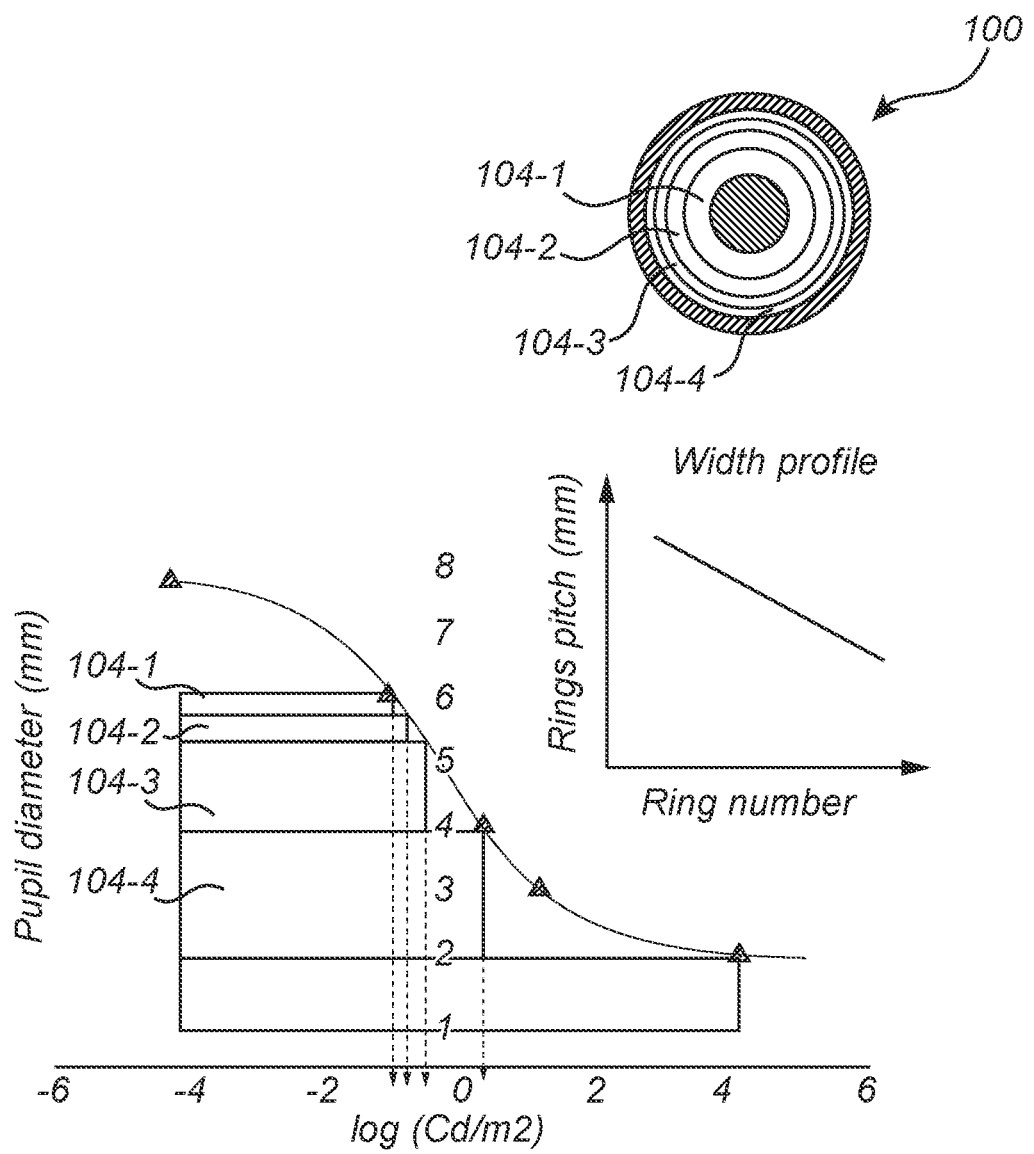
FIG. 5 schematically illustrates a width profile of concentric rings of liquid crystals of an artificial iris according to a third embodiment and user-specific thresholds associated with the rings.
Figure 6:
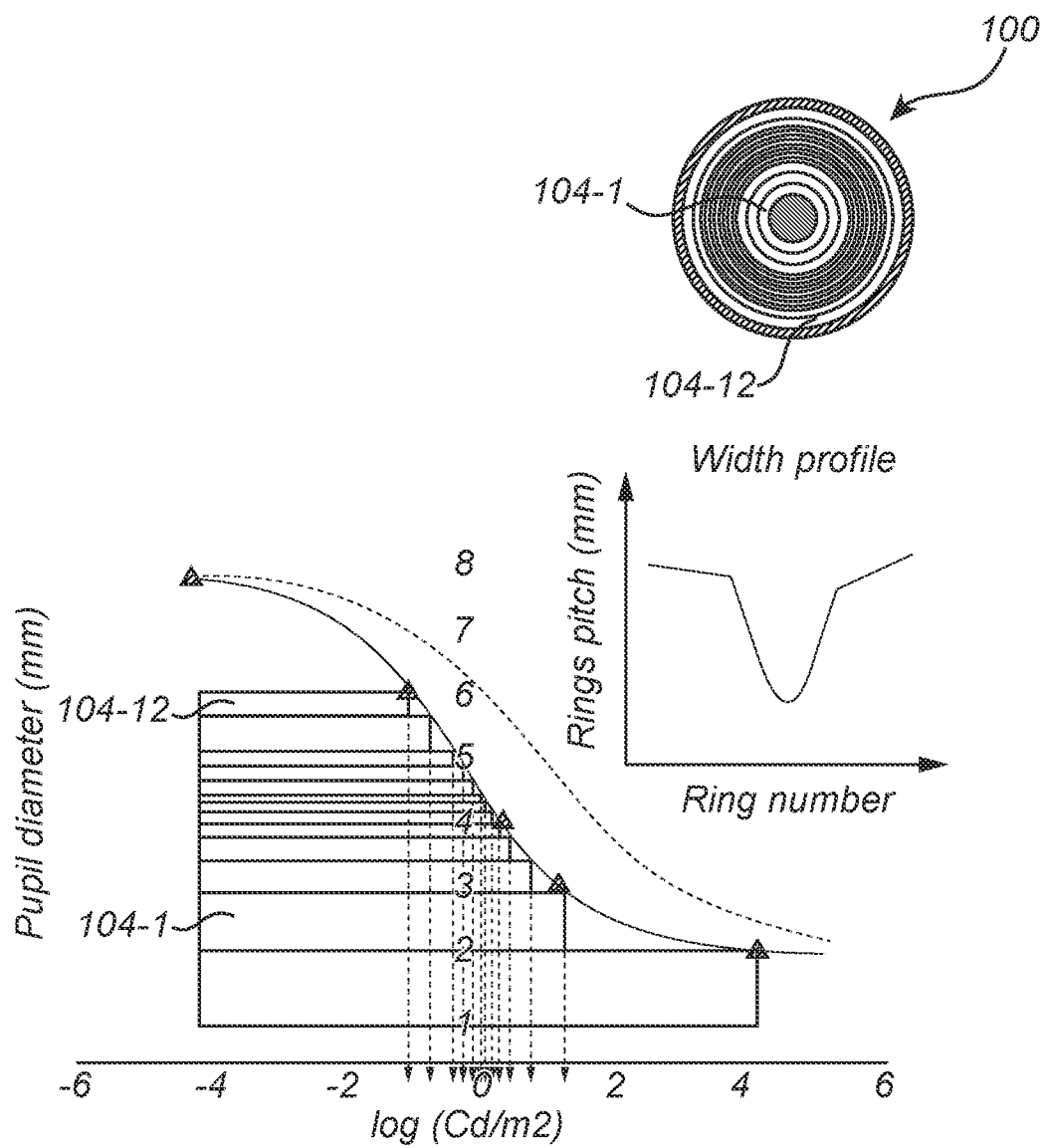
FIG. 6 schematically illustrates a width profile of concentric rings of liquid crystals of an artificial iris according to a fourth embodiment and user-specific thresholds associated with the rings.

The four embodiments of width profiles in FIGS. 3-6 provide widths of the rings being: equidistant (FIG. 3), increasing towards outer rings (FIG. 4), decreasing towards outer rings (FIG. 5) and fine-tuned around a pupil diameter of 5 mm (FIG. 6). In all cases, the dashed lines point out the threshold luminance levels (cd/m$^2$) at which each concentric ring should be turned ON (set to a blocking state) in order to have a pupil diameter corresponding to the user's calibration curve (solid curve).

Figure 3:
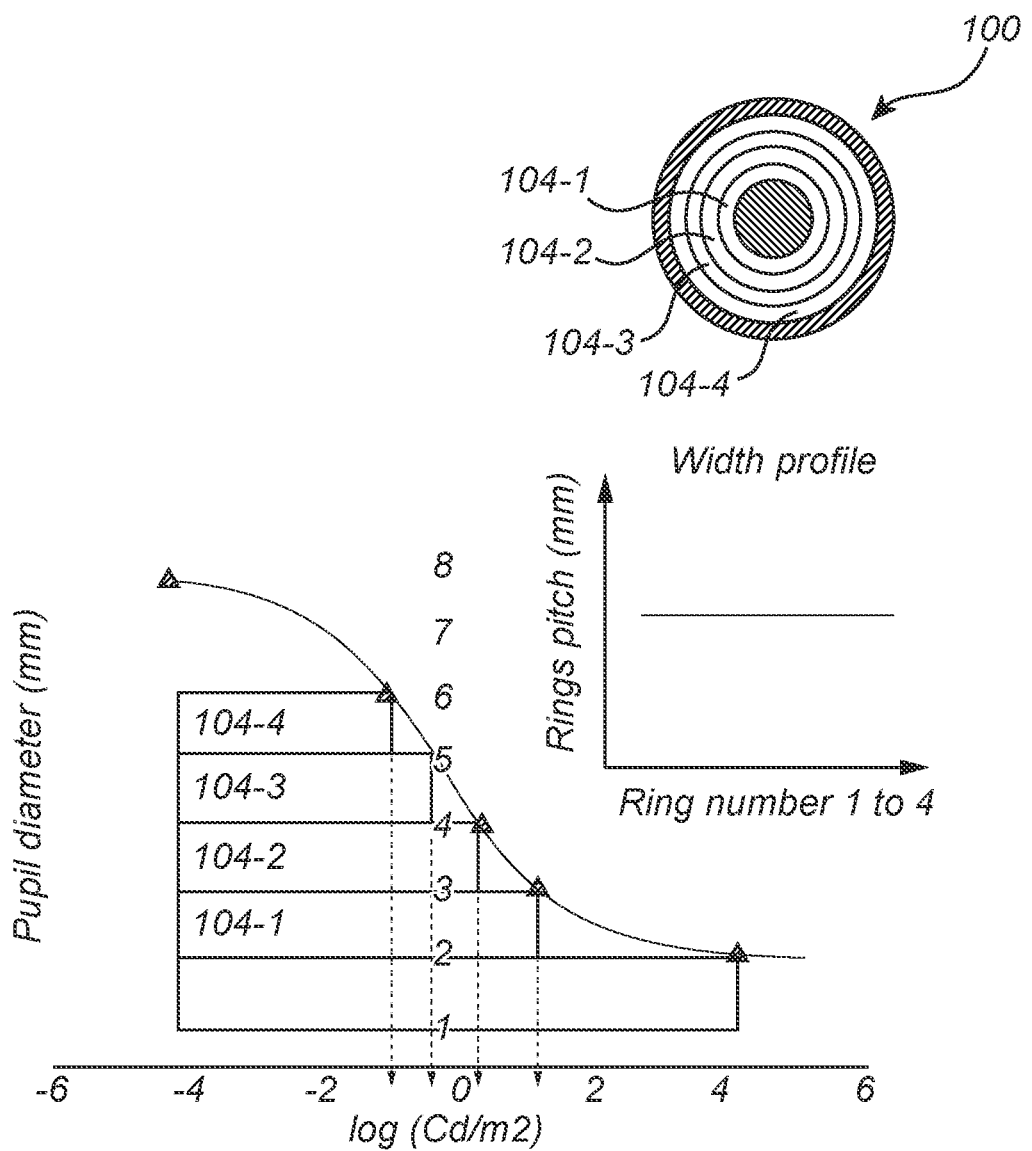
FIG. 3 schematically illustrates a width profile of concentric rings of liquid crystals of an artificial iris according to a first embodiment and user-specific thresholds associated with the rings.

FIG. 3 shows an embodiment with equidistant width pitch from 2 mm to 6 mm for four concentric rings 104-1 to 104-4. The shaded area below the curve indicates the size of the artificial iris 100 that will be used for different luminance levels. FIG. 3 also shows a schematic view of the rings 104-1 to 104-4 as arranged on the artificial iris 100 and a diagram of the relation of ring pitch to ring number to illustrate the set-up of the artificial iris 100 in the embodiment.

The user-specific thresholds are set to reach the user's calibration curve corresponding to the pupil diameter defined by the outer boundary of the respective rings. Thus, the size of the artificial iris 100 will never be larger than a desired pupil diameter as defined by the user's calibration curve. However, it should be realized that the user-specific thresholds may be set in another manner, such as setting the user-specific threshold to reach the user's calibration curve corresponding to a pupil diameter at a center of the width of the respective ring.

The threshold values of illuminance levels in lux for each ring in an example of using equidistant rings as illustrated in FIG. 3 are: 0.09, 0.79, 1.94 and 14.03, respectively. It can be seen that for this example, the equidistant width generates most of the user-specific threshold values at relatively low illuminances, which could be difficult to correctly detect by the light sensor 110.

FIG. 4 shows an embodiment with increasing width pitch from 2 mm to 6 mm for four concentric rings 104-1 to 104-4. The shaded area below the curve indicates the size of the artificial iris 100 that will be used for different luminance levels. FIG. 4 also shows a schematic view of the rings 104-1 to 104-4 as arranged on the artificial iris 100 and a diagram of the relation of ring pitch to ring number to illustrate the set-up of the artificial iris 100 in the embodiment.

The user-specific thresholds are set to reach the user's calibration curve corresponding to the pupil diameter defined by the outer boundary of the respective rings. This type of set-up can be advantageously used for users with higher light sensitivity, since the effective pupil diameter would be smaller for a given low luminance, while it is fine-tuned for higher luminance.

The threshold values of illuminance levels in lux for each ring in an example of using increasing width pitch profile as illustrated in FIG. 4 are: 0.31, 5.99, 314.16 and 4047.15, respectively. For this example, the increasing width profile generates more distributed user-specific thresholds for the illuminance, which could be easier to detect by the light sensor 110.

FIG. 5 shows an embodiment with decreasing width pitch from 2 mm to 6 mm for four concentric rings 104-1 to 104-4. The shaded area below the curve indicates the size of the artificial iris 100 that will be used for different luminance levels. FIG. 5 also shows a schematic view of the rings 104-1 to 104-4 as arranged on the artificial iris 100 and a diagram of the relation of ring pitch to ring number to illustrate the set-up of the artificial iris 100 in the embodiment.

The user-specific thresholds are set to reach the user's calibration curve corresponding to the pupil diameter defined by the outer boundary of the respective rings. This type of set-up can be applied for users with lower light sensitivity, since the effective pupil diameter would be larger for a given high luminance, while it is fine-tuned for lower luminance.

The threshold values of illuminance levels in lux for each ring in an example of using decreasing width pitch profile as illustrated in FIG. 5 are: 0.31, 0.99, 2.49 and 5.99 respectively.

FIG. 6 shows an embodiment with fine-tuned pupil diameters around 5 mm, from 2 mm to 6 mm for 12 concentric rings 104-1 to 104-12. The shaded area below the curve indicates the size of the artificial iris 100 that will be used for different luminance levels. FIG. 6 also shows a schematic view of the rings 104-1 to 104-12 as arranged on the artificial iris 100 and a diagram of the relation of ring pitch to ring number to illustrate the set-up of the artificial iris 100 in the embodiment.

The user-specific thresholds are set to reach the user's calibration curve corresponding to the pupil diameter defined by the outer boundary of the respective rings. This type of set-up can be applied for users with for instance optimal contrast sensitivity with pupil diameters between 4 and 5 mm. This option would allow to fine-tune the pupil diameter within that range ensuring that an optimal contrast is provided.

It should be realized that in FIGS. 3-6, the desired pupil diameter is shown as a function of luminance levels, which are related to the light intensity reaching the retina of the eye providing a retinal illuminance. However, the light sensor 110 may not perfectly detect a representation of the retinal illuminance. Therefore, the user-specific thresholds of luminance levels that may be seen in FIGS. 3-6 may need to be corrected in order to provide thresholds that correspond to the detected light intensity by the light sensor 110.

Figure 7:
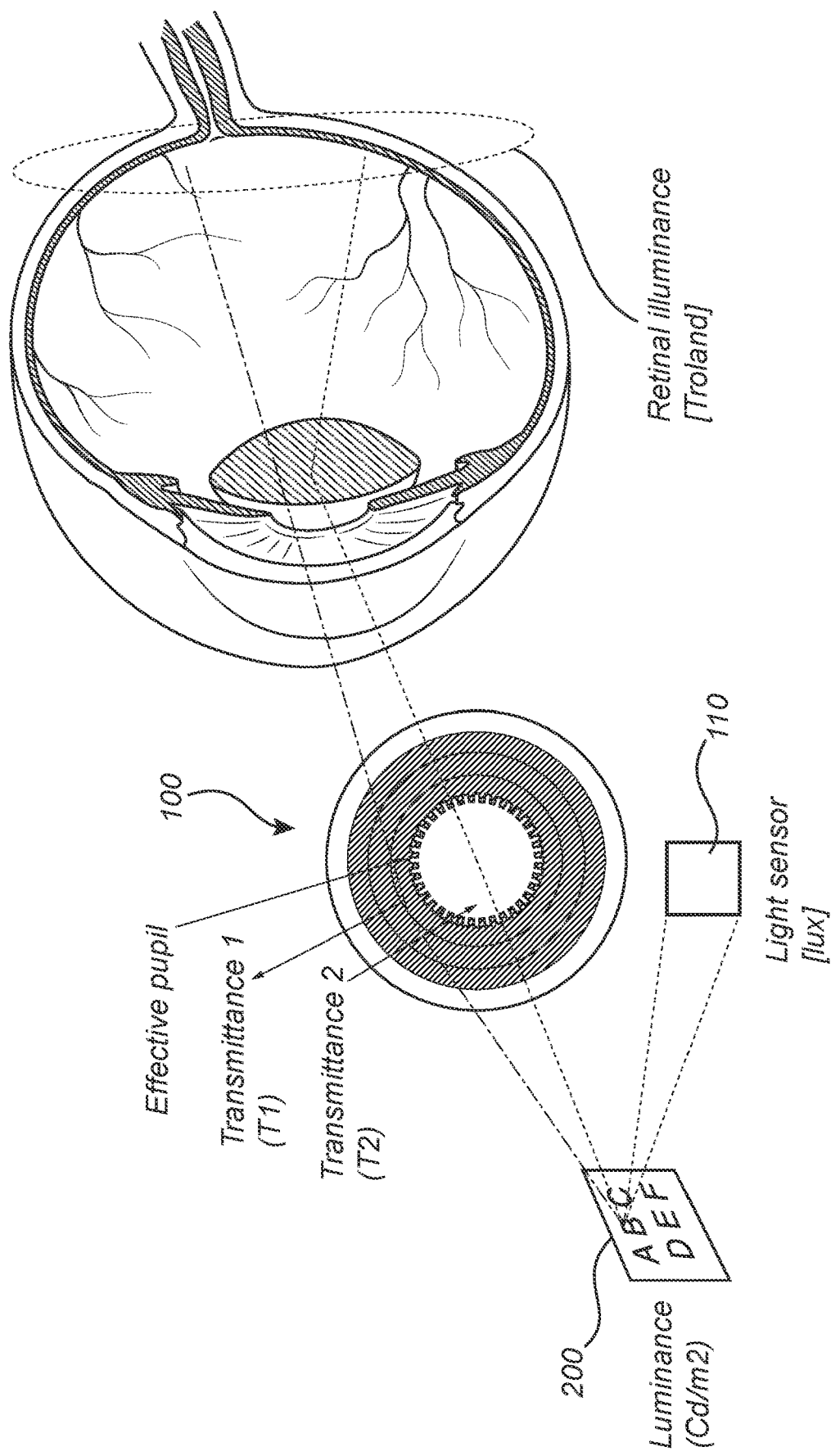
FIG. 7 schematically illustrates light transmittance through an artificial iris for determining user-specific thresholds based on desired retinal illuminance.

Referring now to FIG. 7, determination of user-specific thresholds corresponding to the detected light intensity based on the user calibration will be described.

The user-specific thresholds may define illuminance threshold levels (lux units) measured by the light sensor 110, at which each concentric ring 104-1 to 104-N is actuated ON/OFF (set to blocking/transmitting state) by a specific control circuitry. The user-specific thresholds are set considering the optimal pupil diameter (as discussed above), transmittance of rings 104-1 to 104-N (when ON and OFF) and number of rings already turned ON. Note that even if a ring is turned ON (i.e. set to a blocking state), the ring may still transmit some light.

In order to determine the user-specific thresholds corresponding to the detected light by the light sensor 110, first the luminance values (cd/m²) to which the eye is exposed to, should be converted to illuminance values (lux) measured by the light sensor 110. FIG. 7 illustrates a general concept when converting the luminance to retinal illuminance (and illuminance level detected by the light sensor 110) and the number of rings to be turned ON to achieve the optimal pupil diameter.

A surface source 200 emits a luminance [cd/m²] that is directed to the eye and passing by the artificial iris 100, which blocks some of the light intensity by means of the different transmittance for each ring. The luminance will be measured by the light sensor 110 as an illuminance value [lux]. The light reaching the retina can pass by a turned-ON ring with transmittance T1 and by a turned-OFF ring with a transmittance T2. The more rings turned ON the less light reaching the retina (measured in Troland).

The retinal illuminance corresponding to a luminance level and a particular setting of rings being turned ON and OFF may be described by the equation:

$$\text{Luminance}*\pi*((D\max/2)^2-(D2/2)^2)*T1+\text{Luminance}*\pi*(D2/2)^2*T2,$$

where Dmax is a maximum diameter of the artificial iris 100 (6 mm for the embodiments illustrated in FIGS. 3-6), D2 is the current effective size of the pupil (as defined by the number of rings being currently turned OFF), T1 is the transmittance of rings when turned ON (in blocking state) and T2 is the transmittance of rings when turned OFF.

By multiplying the ratio between the Troland value reaching the retina when the artificial iris 100 is placed in front of the eye versus when it is not, times the luminance level (lux) measured by the light sensor 110, one can calculate the user-specific threshold values at which each ring 104-1 to 104-N should be turned ON in order to follow the user's calibration curve as determined above.

Figure 8:
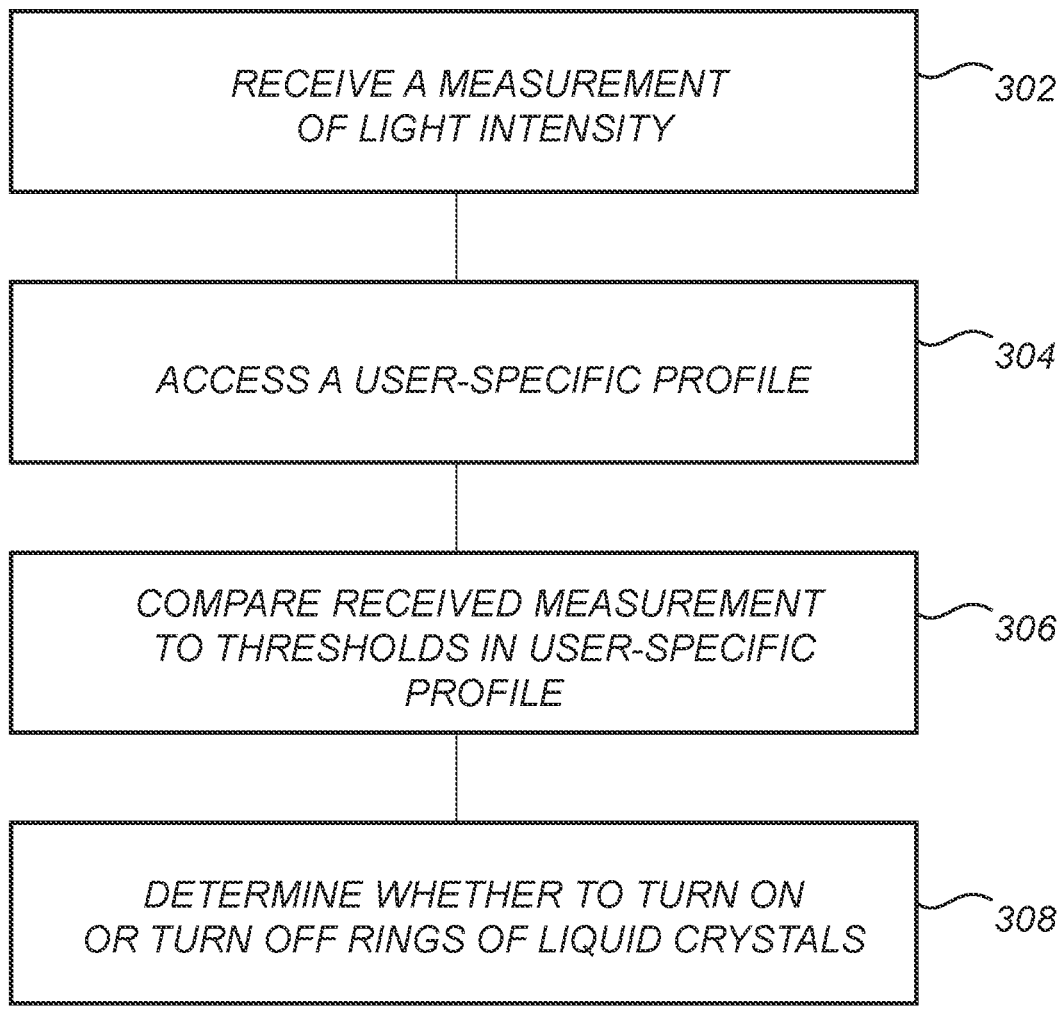
FIG. 8 is a flowchart of a method for controlling an artificial iris according to an embodiment.

Referring now to FIG. 8, a method for controlling an artificial iris 100 using a user-specific profile will be described.

The method may be performed in a processing unit 120, which may be arranged on the carrier 102 of the artificial iris 100. However, the method may alternatively be performed in a processing unit 120 which is external to the artificial iris 100. Thus, processing resources external to the artificial iris 100 may be used so as to prolong battery life of the artificial iris 100.

The use of processing resources external to the artificial iris 100 may also facilitate changing a user-specific profile. However, it should be realized that an update of the user-specific profile may be provided by communication with a wireless communication unit which may be arranged on the carrier 102 of the artificial iris 100.

The control may be based on receiving 302 a measurement of light intensity detected by the light sensor 110. The light sensor 110 may continuously measure the light intensity and transmit measurement results to the processor 122.

The processor 122 may further access 304 a user-specific profile based on user calibration for determining one or more user-specific thresholds of light intensity of the user-specific profile. The processor 122 may access the user-specific profile from a memory 124. The one or more user-specific thresholds are associated with light intensities for triggering a change of a size of the artificial iris 100 through which light is transmitted.

The memory 124 may store more than one user-specific profile, e.g. adapted for control in different conditions or for controlling in relation to optimizing different parameters.

Each user may have a plurality of user-specific profiles. Functionality of the artificial iris 100 may e.g. need to be different if the user is doing exercise, reading, or driving a car. When reading, it may be important that high light intensity levels are received at the retina, which may not be as important when doing exercise (and the user may like not to receive too high light intensities at the retina). In the case of driving a car, the user may be exposed to very fast changes in lighting conditions, e.g. when the car enters or leaves a tunnel.

Thus, by having a plurality of stored user-specific profiles, the artificial iris 100 may be adapted for supporting different functionalities in different lighting conditions and/or in different user situations. This increases versatility of the artificial iris 100.

The input for selecting a stored user-specific profile may be provided by the user. For instance, the user may provide input when the user is about to do a certain activity, such as reading. The input may alternatively be received by the light sensor 110 detecting a change in ambient lighting conditions, which may require a different profile to be used for ensuring a proper functionality of the artificial iris.

The active profile may then be used in controlling the artificial iris 100 for triggering changes of a size of the artificial iris 100 through which light is transmitted. The processor 122 may for instance read the selected user-specific profile into a cache memory for fast access to the user-specific thresholds.

The processor 122 may further compare 306 the received measurement of light intensity to the one or more thresholds in the user-specific profile; and based on said comparing, determine 308 whether to turn on or turn off one or more of the concentric rings 104-1 to 104-N of the artificial iris 100 for controlling an amount of light transmitted through the artificial iris 100.

It should also be realized that the measurement of light intensity may comprise spectral information. Also, the user-specific profile may comprise user-specific thresholds relating to measurements of light for a plurality of wavelengths, such that the control of the artificial iris 100 may be performed in dependence of spectral content of incident light as well as a total intensity of light.

For instance, thresholds relating to blue light may be lower than thresholds relating to other wavelengths, such that the size of the artificial iris 100 may be smaller for large intensities of blue light compared to corresponding intensities of green or red light. This may be used for preventing damage to the retina, since large exposure to blue light can damage light-sensitive cells in the retina.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For example, although single threshold values are discussed above, it should be realized that at least two user-specific thresholds may be associated with triggering a change of the size of the artificial iris 100 using a particular ring 104-1 to 104-N. Thus, a change may be triggered only if the measured light intensity passes both a first threshold value and a second threshold value larger than the first threshold value in the same direction. For instance, if the measured light intensity increases from a value below the first threshold value to a value above the second threshold value, a change may be triggered to turn the corresponding ring ON. Similarly, if the measured light intensity decreases from a value above the second threshold value to a value below the first threshold value, a change may be triggered to turn the corresponding ring OFF. This provides a hysteretic behavior of the control of the artificial iris 100. If for example the measured light intensity were to fluctuate around the first threshold value, an embodiment using hysteretic behavior would provide a more stable way of controlling the artificial iris 100 avoiding very frequent changes to the size of the artificial iris 100 which may be annoying to the user.

The invention claimed is:

1. An artificial iris, said artificial iris comprising:
    a carrier, configured to be arranged in contact with a human eye or implanted in a human eye;
    a plurality of concentric rings of liquid crystals arranged on the carrier, wherein the liquid crystals are switchable between a blocking state providing a low transmittance of light through the artificial iris and a transmitting state providing a high transmittance of light through the artificial iris;
    a sensor arranged on the carrier, for detecting a light intensity incident on the artificial iris; and
    a processing unit comprising a processor and a memory, said memory storing at least one user-specific profile based on user calibration, each user-specific profile being associated with the same user, said processor being configured to:
    receive a measurement of light intensity detected by the sensor;
    access one of the at least one user-specific profile for determining one or more user-specific thresholds of light intensity of the user-specific profile, wherein the one or more user-specific thresholds are associated with light intensities for triggering a change of light transmittance through the artificial iris;
compare the received measurement of light intensity to the one or more thresholds in the user-specific profile; and
determine, based on said comparing, whether to turn on or turn off one or more of the concentric rings of liquid crystals for controlling an amount of light transmitted through the artificial iris,
wherein said processor is configured to receive a measurement of light intensity by receiving measurements of light intensities for a plurality of different wavelength ranges, wherein said user-specific profile comprises one or more user-specific thresholds for each of the plurality of different wavelength ranges, and wherein said processor is configured to compare the received measurement of light intensity to the one or more thresholds in the user-specific profile by comparing each of the measurements of light intensities for a plurality of different wavelengths to the one or more thresholds for each of the plurality of different wavelength ranges in the user-specific profile.

2. The artificial iris according to claim 1, wherein a width of one or more of the plurality of concentric rings is based on user calibration.

3. The artificial iris according to claim 2, wherein the width of the concentric rings is non-equal.

4. The artificial iris according to claim 3, wherein the width of the concentric rings is increasing towards outer rings.

5. The artificial iris according to claim 1, wherein said at least one user-specific profile comprises a plurality of stored user-specific profiles, and wherein said processor is configured to receive input for selecting one of said plurality of stored user-specific profiles to be active, and wherein said access comprises accessing the user-specific profile selected to be active.

6. The artificial iris according to claim 1, wherein said processor is configured to receive input for changing the user-specific profile by changing one or more user-specific thresholds of the user-specific profile.

7. A method for determining a user-specific profile for the artificial iris of claim 6, said method comprising:
receiving user-specific results of optimal pupil diameter for a plurality of different light intensities;
fitting the user-specific results to form a representation of desired pupil diameter in relation to light intensity; and
wherein the one or more user-specific thresholds includes a plurality of user-specific thresholds and said method further comprising determining the plurality of user-specific thresholds forming the user-specific profile, each user-specific threshold defining a minimum light intensity at which each concentric ring is to be turned on providing a low transmittance of light through the artificial iris, wherein each of the user-specific thresholds is determined based on using the formed representation to determine a light intensity associated with a pupil diameter corresponding to the concentric ring being turned on.

8. The method according to claim 7, wherein said fitting comprises determining a hyperbolic tangent function of desired pupil diameter in relation to a logarithm of light intensity, as measured in $Cd/m^2$.

9. The method according to claim 8, wherein each user-specific threshold is determined to represent a threshold light intensity incident on said sensor, said sensor being arranged radially displaced from and adjacent to the concentric rings, said threshold light intensity corresponding to the minimum light intensity being transmitted through the artificial iris when the concentric ring is turned off.

10. The method according to claim 7, further comprising selecting a width of each of the concentric rings based on said user-specific results, said selected widths defining a pupil diameter corresponding to each of the concentric rings.

11. The method according to claim 7, further comprising selecting a set-up of widths of the concentric rings from a plurality of default set-ups based on said user-specific profiles.

12. The method according to claim 7, said method comprising receiving at least two sets of user-specific results of optimal pupil diameter for a plurality of different light intensities, each of the at least two sets representing a different condition for the same user; performing the fitting and the determining for each of the at least two sets of user-specific results to form plural user-specific profiles for the same user.

13. A method for controlling the artificial iris of claim 1, said method comprising:
receiving the measurement of light intensity detected by the sensor on the artificial iris;
accessing the user-specific profile based on user calibration for determining one or more user-specific thresholds of light intensity of the user-specific profile;
comparing the received measurement of light intensity to the one or more thresholds in the user-specific profile; and
determining, based on said comparing, whether to turn on or turn off one or more of the concentric rings of liquid crystals of the artificial iris for controlling the amount of light transmitted through the artificial iris.

14. The method according to claim 13, wherein the at least one user-specific profile includes a plurality of user-specific profiles, further comprising receiving input for selecting one of the plurality of user-specific profiles to be active, each user-specific profile being associated with a same user, wherein said accessing comprises accessing the user-specific profile selected to be active.

15. The method according to claim 13, further comprising receiving input for changing the user-specific profile by changing one or more user-specific thresholds of the user-specific profile.

16. The method according to claim 13, wherein said receiving comprises receiving measurements of light intensities for the plurality of different wavelength ranges, and wherein said comparing comprises comparing each of the measurements of light intensities for the plurality of different wavelengths to the one or more thresholds for each of the plurality of different wavelength ranges in the user-specific profile.

17. A computer program product comprising computer-readable instructions such that when executed on a processing unit the computer-readable instructions will cause the processing unit to perform the method according to claim 13.

* * * * *